(12) United States Patent
Di Caprio et al.

(10) Patent No.: US 11,712,539 B2
(45) Date of Patent: Aug. 1, 2023

(54) DEVICES FOR ASSISTING WITH ADVANCEMENT OF CATHETERS AND RELATED SYSTEMS AND METHODS

(71) Applicant: QXMedical, LLC, Roseville, MN (US)

(72) Inventors: Fernando Di Caprio, St. Paul, MN (US); Gianfranco Panarello, Mount Royal (CA)

(73) Assignee: QXMedical, LLC, Roseville, MN (US)

( * ) Notice: Subject to any disclaimer, the term of this patent is extended or adjusted under 35 U.S.C. 154(b) by 0 days.

(21) Appl. No.: 16/672,708

(22) Filed: Nov. 4, 2019

(65) Prior Publication Data

US 2020/0129734 A1 Apr. 30, 2020

Related U.S. Application Data

(63) Continuation-in-part of application No. 15/499,194, filed on Apr. 27, 2017, now abandoned.

(60) Provisional application No. 62/756,184, filed on Nov. 6, 2018, provisional application No. 62/328,239, filed on Apr. 27, 2016.

(51) Int. Cl.
*A61M 25/00* (2006.01)
*A61M 25/01* (2006.01)
*A61M 25/09* (2006.01)

(52) U.S. Cl.
CPC .... *A61M 25/0069* (2013.01); *A61M 25/0075* (2013.01); *A61M 25/0102* (2013.01); *A61M 25/09* (2013.01); *A61M 2025/0081* (2013.01)

(58) Field of Classification Search
CPC .......... A61M 25/0069; A61M 25/0075; A61M 25/0102; A61M 25/09; A61M 25/01; A61M 25/008; A61M 25/006; A61M 25/0074; A61M 2025/0081
See application file for complete search history.

(56) References Cited

U.S. PATENT DOCUMENTS

| | | | |
|---|---|---|---|
| 5,466,222 A | 11/1995 | Ressemann et al. |
| 5,499,975 A | 3/1996 | Cope et al. |
| 2004/0260333 A1 | 12/2004 | Dubrul et al. |
| 2008/0243081 A1 | 10/2008 | Nance et al. |
| 2008/0249420 A1 | 10/2008 | Crossman |
| 2010/0121346 A1 | 5/2010 | Simpson et al. |
| 2014/0012281 A1 | 1/2014 | Wang et al. |
| 2014/0018773 A1 | 1/2014 | Wang et al. |
| 2014/0276618 A1 | 9/2014 | Di Caprio et al. |

(Continued)

FOREIGN PATENT DOCUMENTS

| | | |
|---|---|---|
| JP | 9253215 A | 9/1997 |
| JP | 2007330483 A | 12/2007 |

(Continued)

*Primary Examiner* — Brooke Labranche
(74) *Attorney, Agent, or Firm* — Fredrikson & Byron, P.A.

(57) ABSTRACT

Disclosed herein is a catheter advancement device having an elongate shaft and a capsule attached to or integral with the shaft, and related methods for assisting with advancement of catheters such as cardiovascular guiding catheters while reducing damage to the inner wall of the blood vessel. Some capsules have a distal plug portion and a neck portion having a smaller diameter than the plug. Other capsules have a channel defined along the outer surface of the capsule. Some elongate shafts have an attachment tube disposed at or near the proximal end thereof.

20 Claims, 7 Drawing Sheets

(56) References Cited

U.S. PATENT DOCUMENTS

| | | | |
|---|---|---|---|
| 2014/0358123 A1* | 12/2014 | Ueda | A61M 25/0053 604/510 |
| 2015/0246209 A1 | 9/2015 | Holzer | |
| 2017/0095646 A1 | 4/2017 | Norman et al. | |
| 2017/0333681 A1 | 11/2017 | Di Caprio et al. | |
| 2018/0280665 A1 | 10/2018 | Di Caprio et al. | |

FOREIGN PATENT DOCUMENTS

| | | |
|---|---|---|
| JP | 2011030615 A | 2/2011 |
| WO | 1997030746 A1 | 8/1997 |
| WO | 2013142386 A1 | 9/2013 |

\* cited by examiner

DEVICES FOR ASSISTING WITH ADVANCEMENT OF CATHETERS AND RELATED SYSTEMS AND METHODS

CROSS-REFERENCE TO RELATED APPLICATION(S)

This application claims the benefit under 35 U.S.C. § 119(e) to U.S. Provisional Application 62/756,184, filed Nov. 6, 2018 and entitled "Improved Catheter Advancement Device," and further claims priority as a continuation-in-part application to U.S. application Ser. No. 15/499,194, filed Apr. 27, 2017 and entitled "Devices for Assisting with Advancement of Catheters and Related Systems and Methods," which claims the benefit under 35 U.S.C. § 119(e) to U.S. Provisional Application 62/328,239, filed Apr. 27, 2016 and entitled "Devices for Assisting with Advancement of Guiding Catheters and Related Systems and Methods," all of which are hereby incorporated herein by reference in their entireties.

FIELD

The various embodiments herein relate to advancement devices for assisting with advancement of a catheter through a blood vessel, including a tortuous or narrow blood vessel, while reducing the risk of damaging the inner wall of the blood vessel with the distal end of the catheter.

BACKGROUND

A guiding catheter (or "sheath") is a standard catheter that is generally a long tube with a pre-determined shape. It is typically used to gain access to the vasculature—such as a coronary artery—by advancing the catheter through the access point during an interventional procedure. The pre-determined, typically curved shape of the catheter facilitates accessing a specific branch or other portion of the vasculature that requires such a curvature in the catheter.

One disadvantage of a pre-shaped, curved distal end of a catheter (including, but not limited to, a guiding catheter or sheath) is that the advancement of the catheter can be impeded by the distal end contacting and damaging the inner wall of the vessel through which the catheter is being advanced. For example, as depicted in FIG. 1A, the pre-shaped distal end 12 of the guiding catheter 10 can potentially contact the inner wall 16 of the blood vessel 14 (at the area A as shown) as the catheter 10 is advanced distally through the vessel 14 (typically over a guidewire such as the guidewire depicted in FIGS. 1B and 1C, which can be, for example, a 0.035" or 0.038" guidewire), thereby scraping or otherwise causing damage to the inner wall 16. This scraping (or other damage) of the inner wall of the blood vessel by the catheter distal end 12 is sometimes called a "razor effect."

As best shown in FIG. 1B, one standard, known technique for overcoming the "razor effect" has been the use of a balloon catheter, such as the balloon catheter 20 as shown in the figure. For example, in use, the balloon catheter 20 can be advanced through the inner lumen 24 of the guiding catheter 10 (or other type of catheter or sheath), positioned such that the balloon 22 is protruding from the #3122009 distal end of the catheter 10 such that a portion of the balloon 22 is positioned within the distal end of the catheter 10 and a portion extends out of the distal end of the catheter 10, and then the balloon 22 is inflated. Once the balloon 22 is inflated, the guiding catheter 10 can be advanced through the blood vessel 14 with the balloon 22 positioned to prevent direct contact between the distal end of the catheter 10 and the inner wall 16 of the vessel 14, thereby preventing the "razor effect." Once the catheter 10 is advanced to the desired position, the balloon 22 is deflated and the balloon catheter 20 is withdrawn from the guiding catheter 10 so that the guiding catheter 10 is ready for use. It is understood that any balloon catheter discussed herein can be any known balloon catheter, including, for example, a percutaneous transluminal coronary angioplasty ("PTCA") balloon catheter.

One disadvantage of using a balloon catheter (such as catheter 20 discussed above) to prevent the razor effect is the cost: balloon catheters are expensive. Another disadvantage is that the positioning of a balloon catheter at the distal end of the guiding catheter makes it difficult to inject any contrast or other fluid through the guiding catheter and past the inflated balloon of the balloon catheter. That is, the balloon must be deflated in order to allow for injection and then re-inflated. An additional disadvantage is that most known balloon catheters (including most PTCA balloon catheters) require the exchange of guidewires in the middle of the procedure. That is, most known balloon catheters in the required size range are only compatible with 0.014" guidewires and thus, during the procedure described above, the surgeon is required to remove the 0.035" or 0.038" guidewire used to insert the pre-shaped catheter and replace it with an 0.014" guidewire in order to be able to introduce the known balloon catheter.

Another disadvantage relates to the use of a advancement device and the tension during introduction of the guide catheter between the need to attach the attachment device to the guide catheter and the need to be able to move the catheter in relation to the guidewire. That is, in use as best shown in FIG. 1C, the guiding catheter 10 is typically positioned within the blood vessel of the patient by first introducing a guidewire 18 and then advancing the catheter 10 over the stationary guidewire 18. To accomplish this, the proximal valve 26 of the catheter 10 has an open configuration such that the guidewire 18 can pass through the valve 26 while allowing the passage of as little fluid as possible (in contrast to its closed configuration in which the valve 26 is fixedly coupled to the guidewire 18 and creates a fluidic seal therebetween). However, it is desirable to attach an advancement device (not shown) to the catheter 10 during advancement by closing the valve 26 to attach it to the advancement device such that the advancement device cannot move in relation to the catheter 10 during advancement. Thus, the need to have the catheter 10 attached to an advancement device combined with the need to have the catheter 10 not attached to the guidewire 18 creates a complication.

Thus, there is a need in the art for an improved method and device for advancing a guiding catheter.

BRIEF SUMMARY

Discussed herein are various catheter insertion or advancement devices for use in assisting with advancement of a catheter through a blood vessel while reducing damage to the inner wall of the blood vessel.

In Example 1, a catheter advancement assistance device comprises an elongate shaft, a capsule fixedly attached to a distal end of the elongate shaft, and an attachment tube associated with a proximal portion of the elongate shaft. The capsule comprises a guidewire lumen defined through the capsule, and an outer diameter substantially similar to an inner diameter of a catheter such that the capsule is sized to be positionable through the catheter.

Example 2 relates to the device according to Example 1, wherein the attachment tube further comprises a tube body, a lumen defined within the tube body, a distal opening defined in a distal end of the tube body, wherein the distal opening is in fluidic communication with the lumen, and a proximal opening defined in a proximal end of the tube body, wherein the proximal opening is in fluidic communication with the lumen.

Example 3 relates to the device according to Example 1, wherein the attachment tube is a compressible attachment tube.

Example 4 relates to the device according to Example 3, wherein the compressible attachment tube comprises an elongate opening defined along a length of the compressible attachment tube.

Example 5 relates to the device according to Example 1, wherein the capsule further comprises a distal portion, and a neck extending proximally from the distal portion, wherein the neck has a smaller diameter than the distal portion.

Example 6 relates to the device according to Example 1, wherein the guidewire lumen has an inner diameter that is larger than an outer diameter of a standard guidewire.

Example 7 relates to the device according to Example 1, wherein the guidewire lumen is sized to allow fluid to flow through the lumen when a standard guidewire is positioned therein.

Example 8 relates to the device according to Example 1, wherein the capsule further comprises a channel defined longitudinally along an outer surface of the capsule.

Example 9 relates to the device according to Example 1, wherein the capsule further comprises a lip formed around at least a portion of an outer circumference of the capsule.

Example 10 relates to the device according to Example 9, wherein the lip comprises at least two lip segments formed around the outer circumference of the capsule.

Example 11 relates to the device according to Example 1, wherein the capsule further comprises an expanded distal section, wherein the expanded distal segment is substantially elastic, a non-expanded proximal section having a smaller diameter than the expanded distal section, and a lip formed at a juncture between the expanded distal section and the non-expanded proximal section, wherein the lip is formed around at least a portion of a circumference of the capsule.

Example 12 relates to the device according to Example 1, wherein the capsule further comprises a substantially elastic ridge formed around at least a portion of an outer circumference of the capsule.

Example 13 relates to the device according to Example 12, wherein the substantially elastic ridge comprises at least two substantially elastic rig segments formed around the outer circumference of the capsule.

Example 14 relates to the device according to Example 1, wherein the capsule further comprises a slot defined in a distal end of the capsule, whereby the distal end of the capsule is compressible.

Example 15 relates to the device according to Example 1, wherein the capsule further comprises a void defined in a portion of the capsule, whereby an area of the capsule near the void is compressible.

In Example 16, a catheter advancement assistance device comprises a push rod, a body fixedly attached to a distal end of the push rod, and a compressible attachment tube associated with a proximal portion of the push rod. The body comprises a distal plug portion, a proximal neck portion, wherein the proximal neck portion has a smaller diameter than the distal plug portion, and a guidewire lumen defined through the body.

Example 17 relates to the device according to Example 16, wherein the guidewire lumen is sized to allow fluid to flow through the lumen when a standard guidewire is positioned therein.

Example 18 relates to the device according to Example 16, wherein the body further comprises a channel defined longitudinally along an outer surface of the body.

Example 19 relates to the device according to Example 16, wherein the body further comprises a seating component formed around at least a portion of an outer circumference of the capsule.

Example 20 relates to the device according to Example 19, wherein the seating component comprises a lip or a ridge.

Example 21 relates to the device according to Example 16, wherein the compressible attachment tube comprises an elongate opening defined along a length of the compressible attachment tube.

In Example 22, a method of assisting advancement of a catheter through a blood vessel comprises inserting an advancement assistance device into a lumen of the catheter, the advancement assistance device comprising an elongate shaft, a body fixedly attached to a distal end of the elongate shaft, and an attachment tube associated with a proximal portion of the elongate shaft. The body comprises a distal plug portion, a proximal neck portion, wherein the proximal neck portion has a smaller diameter than the distal plug portion, and a guidewire lumen defined through the body. The method further comprises urging the advancement assistance device distally into the lumen of the catheter until a distal portion of the distal plug portion extends out of a distal opening in the catheter, a proximal portion of the distal plug portion is positioned within the lumen of the catheter, and the attachment tube is disposed within a proximal valve of the catheter, attaching the proximal valve to the attachment tube, urging the catheter distally into the blood vessel to a target site over a guidewire, and retracting the advancement assistance device from the catheter.

Example 23 relates to the method according to Example 22, further comprising urging the advancement assistance device distally until the distal plug portion extends out of the distal opening, whereby space is provided between the body and the distal opening, urging contrast solution distally through the catheter and through the space between the body and the distal opening and into the blood vessel, and urging the advancement assistance device proximally until the distal portion of the distal plug portion extends out of the distal opening in the catheter and the proximal portion of the distal plug portion is positioned within the lumen of the catheter.

In Example 24, a method of assisting advancement of a catheter through a blood vessel comprises inserting an advancement assistance device into a lumen of the catheter, the advancement assistance device comprising an elongate shaft, a body fixedly attached to a distal end of the elongate shaft, the body comprising a guidewire lumen defined through the body, and an attachment tube associated with a proximal portion of the elongate shaft. The method further comprises urging the advancement assistance device distally into the lumen of the catheter until a distal portion of the body extends out of a distal opening in the catheter, a proximal portion of the body is positioned within the lumen of the catheter, and the attachment tube is disposed within a proximal valve of the catheter, attaching the proximal valve to the attachment tube, urging the catheter distally into the blood vessel to a target site over a guidewire, and retracting the advancement assistance device from the catheter.

Example 25 relates to the method according to Example 24, further comprising urging contrast solution distally through the catheter and through the guidewire lumen and into the blood vessel.

Example 26 relates to the method according to Example 24, wherein the body further comprises a channel defined longitudinally along an outer surface of the body.

Example 27 relates to the method according to Example 26, further comprising urging contrast solution distally through the catheter and through the channel and into the blood vessel.

Example 28 relates to the method according to Example 24, wherein the body further comprises a seating component formed around at least a portion of an outer circumference of the body.

Example 29 relates to the method according to Example 28, wherein the seating component comprises a lip or a ridge.

Example 30 relates to the method according to Example 28, further comprising urging the advancement assistance device distally through the lumen of the catheter until the seating component is urged out of the distal opening in the catheter, and urging the advancement assistance device proximally until the seating component contacts the distal end of the catheter.

Example 31 relates to the method according to Example 24, wherein the attachment tube is a compressible attachment tube, wherein the attaching the proximal valve to the attachment tube causes the compression of the compressible attachment tube.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed or contemplated herein relate to catheter assertion or advancement devices and related methods for assisting in the advancement of a cardiovascular catheter through a blood vessel, including, for example, a cardiovascular guiding catheter or sheath with a curved shape, while reducing or eliminating the risk of damage to the blood vessel inner wall. The various embodiments include a distal capsule and a push rod attached thereto. Alternative embodiments include an attachment tube disposed at a proximal end of the push rod.

Figure 1A:
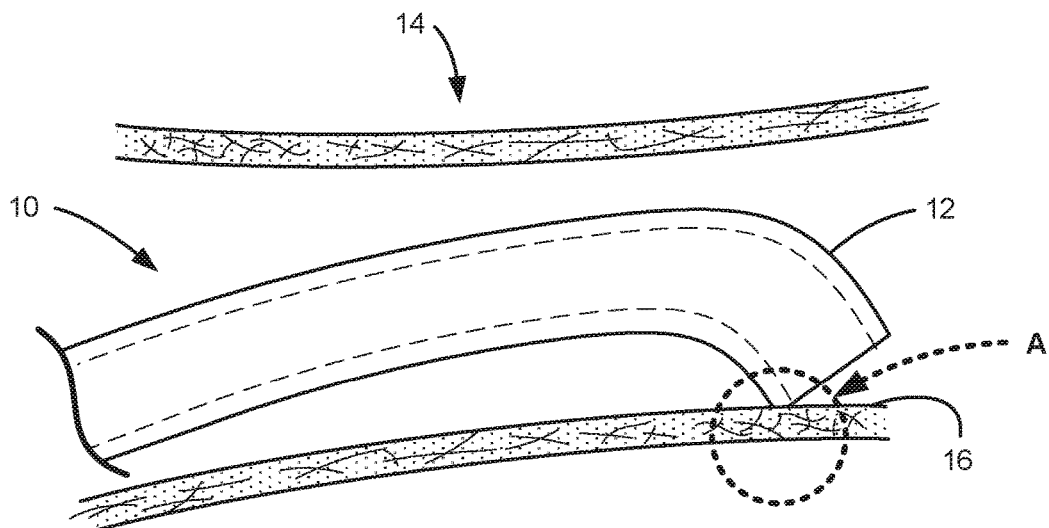
FIG. 1A is a cross-sectional view of a known catheter being advanced through a blood vessel.
Figure 1B:
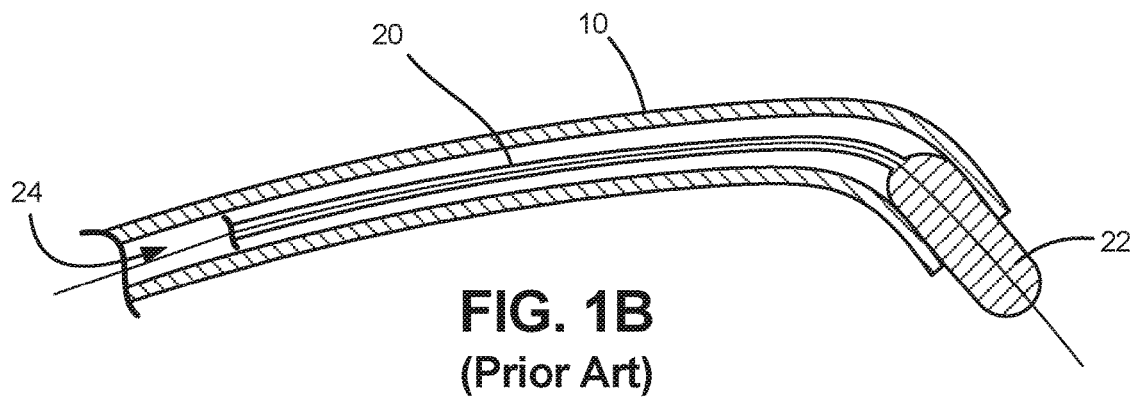
FIG. 1B is a cross-sectional view of a known balloon catheter positioned within a known catheter.
Figure 1C:
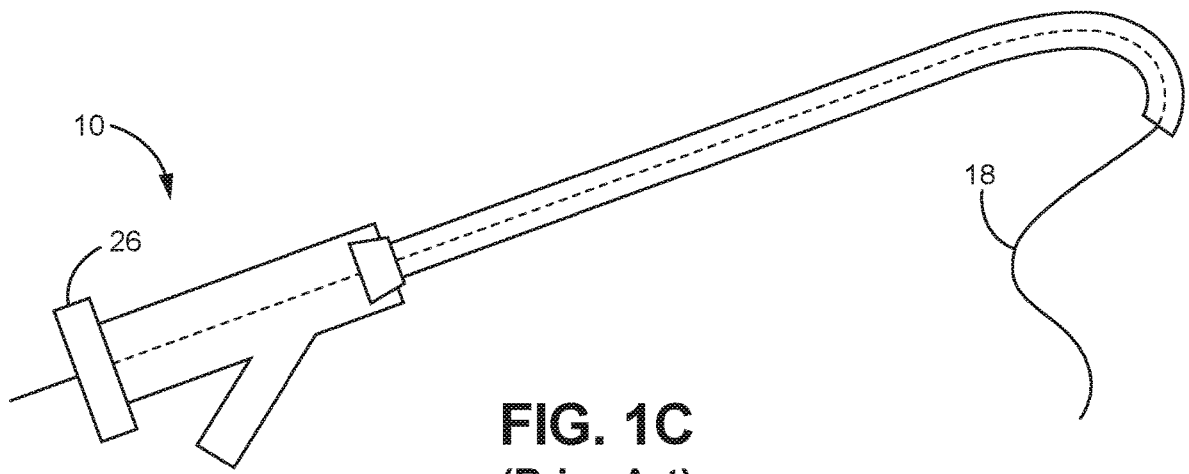
FIG. 1C is a cross-sectional view of a known catheter with a proximal valve.
Figure 2:
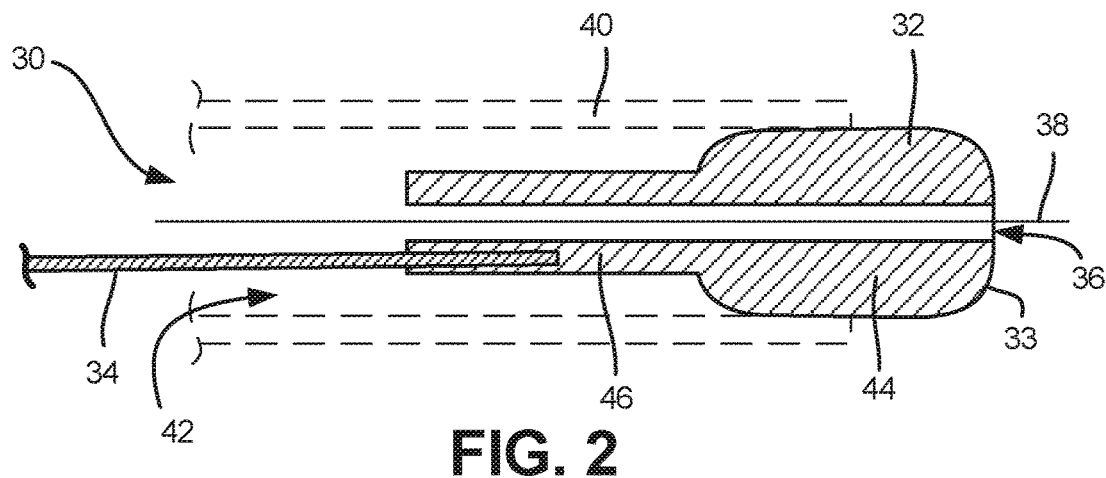
FIG. 2 is a cross-sectional side view of a catheter advancement device positioned within a catheter, according to one embodiment.

FIG. 2 depicts, according to one embodiment, a catheter advancement device 30 (also referred to as an "insertion device," a "catheter insertion device," or an "advancement device") for assisting with or use in advancing a catheter, such as, for example, a guiding catheter. The device 30 has a capsule (also referred to herein as a "body" or "insertion body") 32 with a partially rounded distal end 33 and a push rod (also referred to herein as an "elongate component") 34 coupled thereto. The capsule 32 has a lumen 36 defined therethrough that is configured to allow for passage of a guidewire 38 therethrough as shown. The push rod 34 is embedded in or otherwise fixedly coupled to the capsule 32 such that appropriate forces can be applied at the proximal end of the push rod 34 by a user (such as a surgeon or medical professional) to urge the capsule 32 distally or proximally during use.

In use as shown in the figure, the distal end of the capsule insertion device 30 can be advanced through the inner lumen 42 of a guiding catheter 40 (by a user holding the proximal end of the rod 34) and positioned such that the capsule 32 is protruding from the distal end of the catheter 40. In this position, a portion of the capsule 32 is positioned within the distal end of the catheter 40 and a portion extends out of the distal end of the catheter 40. At this point, the user locks the device 30 into position in relation to the catheter 40. That is, according to one embodiment, the user attaches the proximal end of the rod 34 to the catheter 40 in any known fashion. For example, in one specific implementation, a known locking mechanism at the proximal end of the catheter 40 (such as a Tuohy-Borst adapter, for example) is used to lock the device 30 to the catheter 40. Alternatively, the locking mechanism can be a proximal valve similar to the proximal valve 26 discussed above in the Background. As such, the advancement device 30 is locked or otherwise attached to the catheter 40 such that the device cannot move translationally in relation to the catheter 40. Once the capsule 32 is positioned as shown (and, in some cases, the device 30 is locked in place), the guiding catheter 40 can be advanced through a blood vessel with the capsule 32 positioned to prevent direct contact between the distal end of the catheter 40 and the inner wall of the vessel, thereby preventing the "razor effect." Once the catheter 40 is advanced to the desired position, the capsule catheter 30 is withdrawn from the guiding catheter 40 by a user pulling the push rod 34 in the proximal direction so that the guiding catheter 40 is ready for use.

The capsule body 32 can be a solid body with a lumen 36 defined therethrough as shown. Alternatively, in the various embodiments disclosed or contemplated herein, the capsule (such as capsule 32) can be any component or body that can be inserted through a guiding catheter and positioned to reduce or eliminate the razor effect. According to some embodiments, the capsule is non-inflatable. In certain implementations, the capsule has a substantially cylindrical shape. Alternatively, the capsule can have any known shape that allows it to be advanced through a catheter and positioned out of the distal end thereof as described herein.

In certain embodiments, the outer diameter of the body 32 can vary or have specific features as described herein depending on the desired functionality of the body 32. In this specific implementation, the capsule 32 has a larger distal portion (also referred to herein as a "plug," "distal plug," or "distal body") 44 and a smaller proximal portion (also referred to as a "neck," or "tail") 46. The distal body 44 has a larger diameter than the neck 46. In the embodiment as shown, the capsule 32 is a single integral body 32 having the larger distal portion 44 and the smaller proximal portion 46 as shown. Alternatively, the capsule 32 can have two separate portions coupled together: the first larger distal portion 44 and the second smaller proximal portion 46 attached thereto.

In one embodiment, the capsule 32 has an outer diameter ranging from about 0.05 inches to about 0.3 inches. Alternatively, the outer diameter ranges from about 0.065 inches to about 0.105 inches. In a further implementation, the capsule 32 has an outer diameter that fits snugly within (makes contact with the inner wall of) any cardiovascular guiding catheter, such as, for example, the Medtronic Launcher™ or Cordis VistaBrite™ 5 French to 8 French guiding catheters. Further, the capsule 32 can be sized to fit snugly within any guiding catheter having any size ranging from about 4 French to about 22 French. It is understood that the "snug" fitting in this embodiment and in any other capsule embodiment disclosed or contemplated herein is a fitting of the capsule (such as capsule 32) within the catheter such that the outer surface of the capsule makes sufficient contact with the inner wall of the catheter to prevent passage of fluid therebetween.

In one embodiment, any capsule embodiment disclosed or contemplated herein (such as capsule 32) is made of a polymeric material. For example, the capsule can be made of polyethylene, Pebax, Nylon, polyester, or any other polymeric material or combination thereof. Alternatively, the capsule can also be made of metal or any other known material that can be used for medical devices. In a further implementation, the capsule (such as capsule 32) can be made of two or more materials. More specifically, in certain embodiments, the capsule can be made of two or more materials having differing stiffness and/or flexibility such that one portion of the capsule (such as the distal end, for example) is stiffer, more rigid, and/or less flexible than another portion. In other words, the two or more materials can be used to create a capsule that has stiffness, rigidity, or flexibility that varies along the length of the capsule.

Further, any capsule embodiment disclosed or contemplated herein (such as capsule 32) can also have a coating disposed on the outer surface of the capsule to increase the lubricity of the capsule. In certain implementations, the coating can be hydrophilic or hydrophobic.

According to any embodiment disclosed or contemplated herein, the push rod (such as push rod 34) can be made of metal. Alternatively, the push rod can be made of any known material that can be used to make an elongate component with sufficient column strength such that the component can be used to advance a capsule through the lumen of a guiding catheter while also having some flexibility. It is understood that the push rod (also referred to as a "proximal elongate member" or "control rod" or "manipulation rod") in any embodiment herein can be any elongate component that is coupled to the proximal end of the capsule and can withstand the forces necessary for a user to urge the rod distally or proximally to move the capsule through a guiding catheter as described herein. In certain alternative implementations, the push rod can be integral with the capsule. Further, various embodiments include a push rod and capsule formed together of the same materials such that the push rod is integral with the capsule.

Figure 3A:
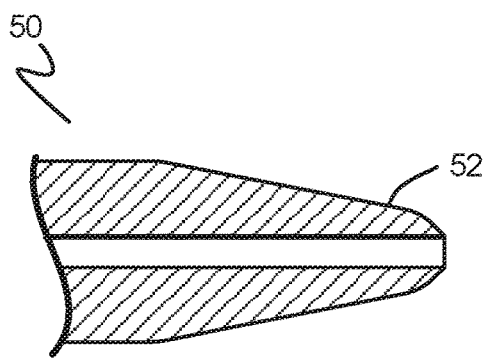
FIG. 3A is a cross-sectional side view of a distal portion of a plug of a catheter advancement device, according to one embodiment.
Figure 3B:
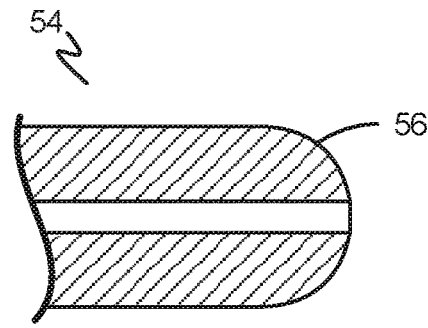
FIG. 3B is a cross-sectional side view of a distal portion of a plug of a catheter advancement device, according to another embodiment.

It is understood that the capsule (such as capsule 32) can take a variety of shapes, so long as the capsule can be positioned out of the distal end of a guiding catheter as described herein and help with advancement thereof through a blood vessel. For example, capsule 50 as best shown in FIG. 3A according to one embodiment has a tapered distal end 52, while capsule 54 as best shown in FIG. 3B in accordance with another implementation has a rounded distal end 56. According to further alternatives, the capsule can have a distal end with an angled shape, a spherical shape, or any other known shape that helps to advance the guiding catheter when the capsule is positioned out of the distal end of the guiding catheter.

Figure 4:
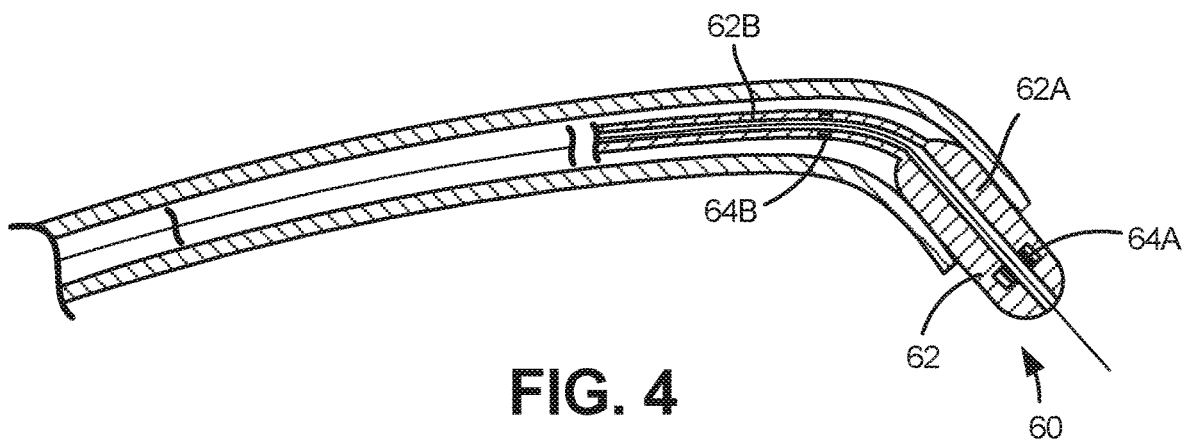
FIG. 4 is a cross-sectional side view of a catheter advancement device having visualization markers and positioned within a catheter, according to one embodiment.

In certain implementations, any advancement device disclosed or contemplated herein can have at least one visualization marker disposed on the device. One exemplary embodiment is depicted in FIG. 4, in which the capsule insertion device 60 has two visualization markers 64A, 64B.

The first visualization marker 64A is disposed at or near the distal end of the distal plug 62A of the capsule 62, while the second marker 64B is disposed on the neck 62B of the capsule 62. Alternatively, any device embodiment can have one marker or three or more markers. It is understood that the markers 64A, 64B (and any markers incorporated into any capsule insertion device embodiment as disclosed or contemplated herein) can be radiopaque markers. Alternatively, the markers (such as markers 64A, 64B) can be made of any known material for a visualization marker. The markers 64A, 64B—and any such markers used in any embodiment herein—can be used to assist a user with positioning the capsule insertion device 60.

In use, it is often necessary or helpful to inject contrast solution through the lumen of a guiding catheter and into the vasculature of the patient to assist with placement of the guiding catheter. As discussed above, if a known balloon catheter is being used to assist with advancement of the guiding catheter, the process for injecting the contrast solution is complicated by the presence of the balloon, which must be deflated in order to inject the solution. However, as best shown in FIGS. 5-7B, various embodiments of the capsule device disclosed or contemplated herein eliminate those complications.

Figure 5:
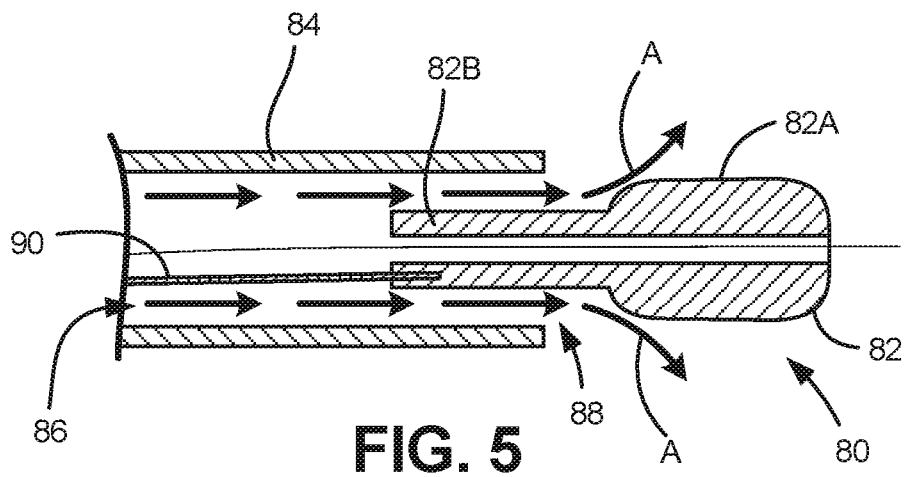
FIG. 5 is a cross-sectional side view of a catheter advancement device extending out of a distal end of a catheter, according to one embodiment.

For example, in one implementation as shown in FIG. 5, the catheter advancement device 80 has a capsule 82 with a distal body 82A and a neck 82B similar or identical to the capsule 32 described above. To inject contrast solution after the capsule 82 has been positioned at the distal end of the guiding catheter 84 (for advancing the catheter 84 through the vasculature as described above), the capsule device 80 is urged distally (by a user urging the proximal end of the push rod 90 distally) such that the body 82A of the capsule 82 is urged distally out of the lumen 86 of the guiding catheter 84 as shown in FIG. 5. More specifically, the capsule 82 is urged distally until the body 82A is urged out of the lumen 86 such that space is created between the opening 88 of the guiding catheter 84 and the body 82A, thereby making it possible for contrast to exit from the opening 88 as represented by arrows A. In certain implementations such as that shown in FIG. 5, the capsule 82 need not be urged distally so far that the neck 82B also exits the lumen 86. Instead, the smaller diameter of the neck 82B allows for sufficient space between the neck 82B and the opening 88 to allow for contrast to exit the lumen 86.

Figure 6:
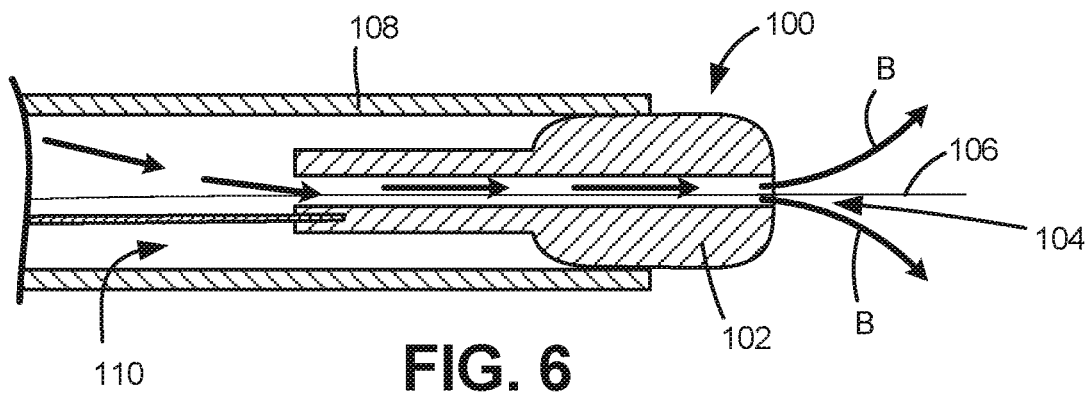
FIG. 6 is a cross-sectional side view of a catheter advancement device positioned within a catheter, according to another embodiment.

In an alternative embodiment, as shown in FIG. 6, the capsule 102 need not be advanced distally out of the lumen 110 of the guiding catheter 108. More specifically, one implementation of a capsule device 100 has a capsule 102 with a lumen 104 defined therein that has a larger inner diameter than is necessary to accommodate solely a guide wire 106. As such, the lumen 104 has a sufficient inner diameter to provide space for the guide wire 106 while also having sufficient additional space to allow for contrast solution to flow distally out of the guiding catheter 108 through the capsule lumen 104 and into the vasculature as represented by arrows B. In one embodiment, the inner diameter of the lumen 104 ranges from about 0.01 inches to about 0.05 inches. Alternatively, the inner diameter ranges from about 0.02 inches to about 0.04 inches. In a further implementation, the inner diameter of the lumen 104 is sufficiently large to receive a guidewire of any size ranging from 0.01 inches to 0.04 inches and still has at least a 0.004 inch diameter of space between the guidewire and the inner wall of the lumen 104.

In use, once the capsule device 100 is positioned at the distal end of the guiding catheter 108 such that the capsule 102 is positioned as desired for advancing the catheter 108, the capsule 102 need not be moved in order to inject the contrast solution. Instead, the capsule 102 can remain in place while the contrast solution flows distally through the lumen 110 of the guiding catheter 108 and through the lumen 104 of the capsule 102 and out into the vasculature.

Figure 7A:
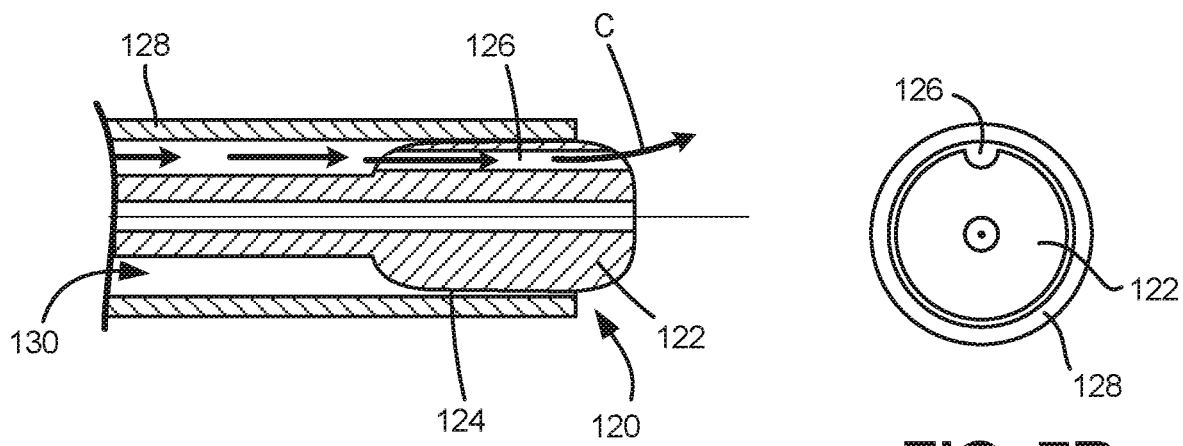
FIG. 7A is a cross-sectional side view of a catheter advancement device positioned within a catheter, according to a further embodiment.
Figure 7B:
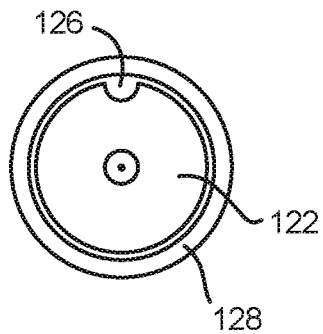
FIG. 7B is a cross-sectional front view of the catheter advancement device of FIG. 7A.

Another configuration as depicted in FIGS. 7A and 7B also allows for contrast solution injection without moving the capsule device. In this implementation, the capsule device 120 has a capsule 122 with a channel (also referred to as a "slot" or "trough") 126 defined longitudinally along the outer surface 124 of the capsule 122 (as best shown in FIG. 7B). As such, the channel 126 defines a space between the capsule 122 and the inner surface of the lumen 130 of the guiding catheter 128 through which contrast solution can flow distally out into the vasculature as represented by arrows C. In one embodiment, the channel 126 has an inner diameter ranging from about 0.002 inches to about 0.02 inches. Alternatively, the inner diameter ranges from about 0.004 inches to about 0.008 inches. In use, once the capsule device 120 is positioned at the distal end of the guiding catheter 128 such that the capsule 122 is positioned as desired for advancing the catheter 128, the capsule 122 need not be moved in order to inject the contrast solution. Instead, the capsule 122 can remain in place while the contrast solution flows distally through the lumen 130 of the guiding catheter 128 and through the channel 126 of the capsule 122 and out into the vasculature. It is understood that, according to various alternatives, the channel 126 can be any feature or configuration on the capsule 122 or the outer surface 124 thereof that allows fluid flow between the capsule 122 and the inner wall of the lumen 130.

Both the larger lumen 104 of the capsule device 100 embodiment and the channel 126 of the capsule device 120 implementation make it easy for a user to inject contrast solution, as discussed above. In addition, these two embodiments can also assist with limiting contrast fluid use. Injection of excess contrast fluid into the vasculature of a patient during an interventional procedure can cause health issues for the patient, including contrast-induced nephropathy. The lumen 104 of a predetermined diameter in the device 100 embodiment or the channel 126 of a predetermined depth or diameter in the device 120 embodiment both provide mechanisms for injecting solution in known, more limited amounts than those injected when using a balloon catheter as described above.

In certain alternative implementations, another capsule is provided—for use with any of the capsule device embodiments disclosed or contemplated herein—that has a seating component defined or disposed around an outer surface of the capsule that can assist with positioning the capsule in relation to the guiding catheter during use and further can create a smoother or more streamlined transition from the outer surface of the capsule to the outer surface of the guiding catheter in which the capsule is positioned. It is understood that any of the seating components disclosed or contemplated herein can be defined or disposed around the entire 360 degree circumference of the capsule. Alternatively, any such components can be defined or disposed around only a portion of the circumference of the capsule. In a further embodiment, any such seating component can be defined or disposed intermittently around the circumference of the capsule such that there are two or more seating components disposed or defined thereon such that they are positioned at different locations along and around the circumference thereof.

Figure 8:
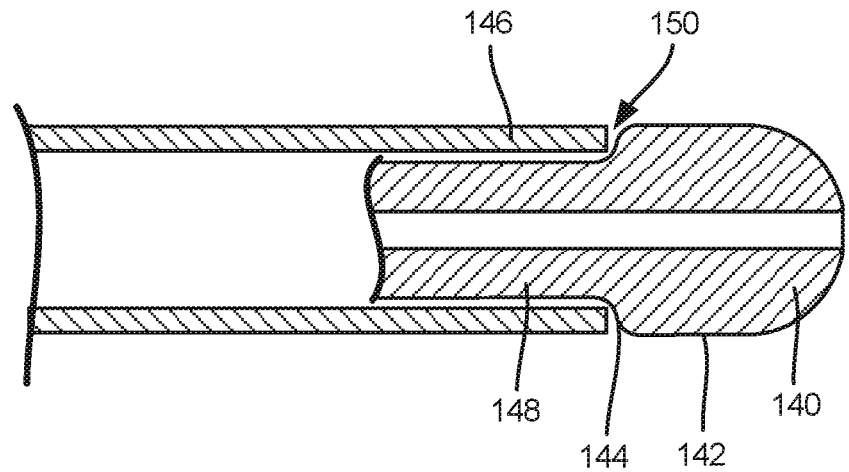
FIG. 8 is a cross-sectional side view of a catheter advancement device positioned within a catheter, according to yet another embodiment.

One example of such a capsule is depicted in FIG. 8, which shows one embodiment of a capsule 140 having a seating component (or "seating feature") 144. In this specific example, the seating component 144 is a lip 144 created by the capsule 140 having an expanded section 142 (which is a portion of the capsule 140 that has an increased diameter in comparison to the rest of the capsule 140). That is, the lip 144 is formed at the juncture of the expanded section 142 and the non-expanded section of the capsule 140. As discussed above, the lip 144 can extend around the entire circumference, can extend around a portion of the circumference, or can constitute two or more lips 144 that are disposed or defined intermittently around the circumference. In one embodiment, the expanded section 142 is a portion of the body 148 of the capsule 140. Alternatively, the expanded section 142 can be the body itself (not shown), and the transition from the body (not shown) to the neck (not shown) constitutes the seating component. The expanded section 142 has an outer diameter that is substantially similar to or the same as the outer diameter of the guiding catheter 146. In certain embodiments, the expanded section 142 or the entire capsule 140 has sufficient elasticity to allow for deformation of the expanded section 142 such that the capsule 140 can be advanced through the guiding catheter 146 despite the expanded section 142 having an outer diameter that is larger than the inner diameter of the guiding catheter 146 lumen. Regardless of the specific embodiment of the capsule with the seating component (such as seating component 144), it is understood that the capsule 140 has at least a portion of its outer surface that fits snugly within the catheter as described elsewhere herein such that no fluid can pass between the outer surface of the capsule 140 and the inner surface of the catheter.

In use, the capsule 140 is advanced distally through the guiding catheter 146 and positioned out of the distal opening 150 of the guiding catheter 146 according the same procedure used for all the capsule device embodiments herein. As mentioned above, the capsule 140 has an expanded section 142 that has elastic characteristics that allow for the section 142 to deform sufficiently as the capsule 140 is advanced through the guiding catheter to allow for passage of the capsule 140 despite the expanded section 142 having a greater diameter than the inner diameter of the lumen of the guiding catheter 146. As the expanded section 142 of the capsule 140 is urged out of the opening 150 at the distal end of the guiding catheter 146, the expanded section 142 expands back to its natural diameter, thereby causing formation of the lip 114. The user can then urge the capsule 140 back in a proximal direction—via the push rod (not shown)—until the lip 114 is in contact with the guiding catheter 146, thereby confirming for the user via increased resistance that the capsule 140 is in the desired position in relation to the guiding catheter 146. It is understood that the user must be aware that she or he cannot use so much force that the expanded section 142 deforms and the capsule 140 is urged proximally past the desired capsule 140 position. Once the capsule 140 is positioned as desired, it can be seen in FIG. 8 that the expanded section 142 has a diameter that is substantially similar to the outer diameter of the guiding catheter 146, thereby reducing the risk of the distal end of the guiding catheter 146 making contact with an inner wall of a blood vessel wall during advancement of the guiding catheter 146. Once the capsule 140 is positioned, the user then advances the guiding catheter 146 via the push rod (not shown).

Figure 9:
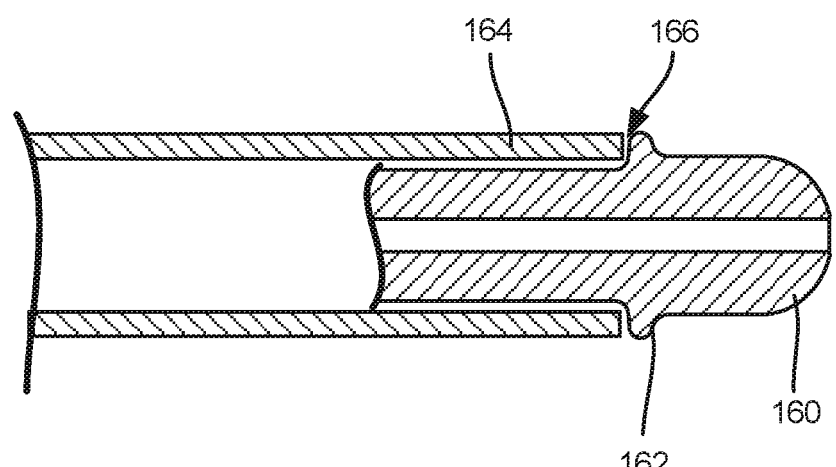
FIG. 9 is a cross-sectional side view of a catheter advancement device positioned within a catheter, according to an alternative embodiment.

Another example of a capsule with a seating component is depicted in FIG. 9, which shows a capsule 160 having a seating component 162. In this specific example, the seating component 162 is a ridge 162 formed or disposed on the outer surface of the capsule 160. As discussed above, the ridge 162 can extend around the entire circumference, can extend around a portion of the circumference, or can constitute two or more ridges 162 that are disposed or defined intermittently around the circumference. The ridge 162 has an outer diameter that is substantially similar to or the same as the outer diameter of the guiding catheter 164. In certain embodiments, the ridge 162 or the entire capsule 160 has sufficient elasticity to allow for deformation of the ridge 162 such that the capsule 160 can be advanced through the guiding catheter 164 despite the ridge 162 having an outer diameter that is larger than the inner diameter of the guiding catheter 164 lumen. As with all capsule implementations herein, regardless of the specific embodiment of the capsule with the seating component (such as seating component 162), it is understood that the capsule 160 has at least a portion of its outer surface that fits snugly within the catheter as described elsewhere herein such that no fluid can pass between the outer surface of the capsule 160 and the inner surface of the catheter.

In use, the capsule 160 is advanced distally through the guiding catheter 164 and positioned out of the distal opening 166 of the guiding catheter 164 according the same procedure used for all the capsule device embodiments herein. As mentioned above, the ridge 162 on the capsule 160 has elastic characteristics that allow for the ridge 162 to deform sufficiently as the capsule 160 is advanced through the guiding catheter 164 to allow for passage of the capsule 160 despite the ridge 162 having a greater diameter than the inner diameter of the lumen of the guiding catheter 164. As the ridge 162 of the capsule 160 is urged out of the opening 166 at the distal end of the guiding catheter 164, the ridge 162 expands back to its natural diameter. The user can then urge the capsule 160 back in a proximal direction until the ridge 162 is in contact with the guiding catheter 164, thereby confirming that the capsule 160 is in the desired position in relation to the guiding catheter 164. It is understood that the user must be aware that the user cannot use so much force that the ridge 162 deforms and the capsule 160 is urged proximally past the desired capsule 160 position. Once the capsule 160 is positioned as desired, it can be seen in FIG. 9 that the ridge 162 has a diameter that is substantially similar to the outer diameter of the guiding catheter 164, thereby reducing the risk of the distal end of the guiding catheter 164 making contact with an inner wall of a blood vessel wall during advancement of the guiding catheter 164. Once the capsule 160 is positioned, the user then advances the guiding catheter 164.

Figure 10A:
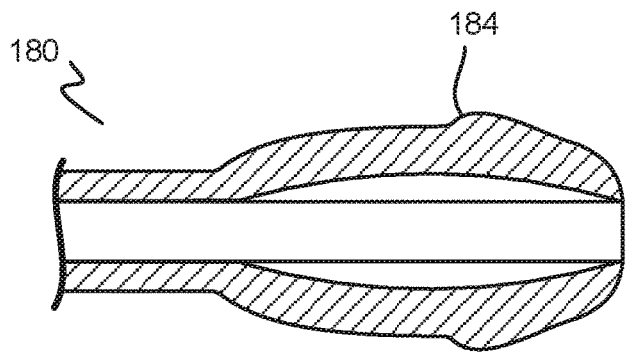
FIG. 10A is a cross-sectional side view of a plug, according to another alternative embodiment.
Figure 10B:
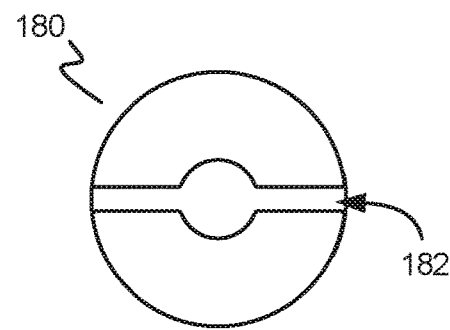
FIG. 10B is a cross-sectional front view of the plug of FIG. 10A.
Figure 11A:
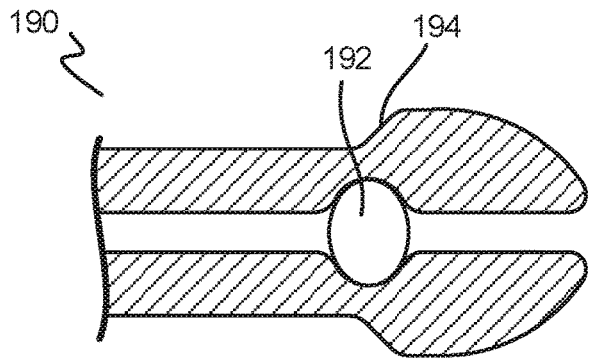
FIG. 11A is a cross-sectional side view of a plug, according to another alternative embodiment.
Figure 11B:
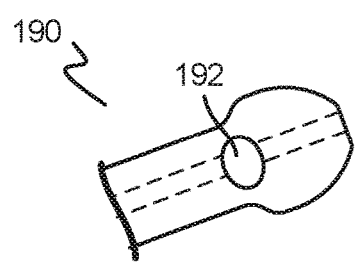
FIG. 11B is a further cross-section side view of the plug of FIG. 11A.

In certain implementations in which the capsule has a seating component (such as the seating components 144, 162 described above, for example) or similar feature, the deformation or partial collapse of the capsule makes it possible for the capsule to advance through the guiding catheter as discussed above. In one exemplary embodiment as shown in FIGS. 10A and 10B, instead of the capsule having elasticity as described above, a capsule 180 is provided that is a deformable or collapsible capsule 180. That is, the capsule 180 has a slot 182 defined in the distal end of the capsule 180 along the length of the capsule 180 that also has a seating component 184 (similar to one of the seating components 144, 162 described above). In use, the slot 182 allows for the capsule 180 to be deformed or have a smaller diameter as it is advanced through a guiding catheter, similar to the use of the capsules 140, 160 discussed above.

In another embodiment, a capsule 190 is provided that is collapsible or deformable as a result of an opening 192 defined at a distal portion of the capsule along the length of the capsule 190 that also has a seating component 194. In use, the opening 192 allows for the capsule 190 to be deformed or have a smaller diameter as it is advanced through a guiding catheter, similar to the use of the capsules 140, 160 discussed above.

As discussed above, it is understood that the seating components 184, 194 described above with respect to FIGS. 10A-11B can extend around the entire circumference, can extend around a portion of the circumference, or can constitute two or more such components that are disposed or defined intermittently around the circumference.

Figure 12:
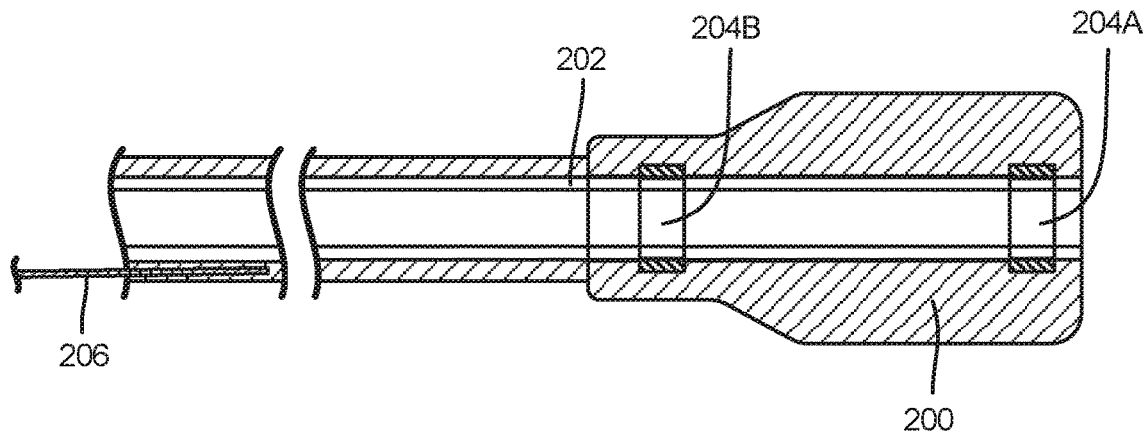
FIG. 12 is a cross-sectional side view of a method of making a catheter advancement device, according to one embodiment.

The various catheter insertion device embodiments disclosed or contemplated herein can be made in any number of known ways. In one embodiment as shown in FIG. 12, a capsule 200 can be formed using an injection molding process. In this process, the starting point is an inner tube 202, with the capsule 200 being injection molded over the inner tube 202. In certain implementations in which the capsule 200 has two marker bands 204A, 204B, the marker bands 204A, 204B are disposed over the inner tube 202 before the capsule 200 is injected molded thereon such that the material for the capsule 200 is injection molded onto the marker bands 204A, 204B, thereby resulting in the marker bands 204A, 204B being embedded in the capsule 200. Further, the push rod 206 can be embedded in the capsule 200 in a similar fashion. That is, the push rod 206 can be positioned along the inner tube 202 such that injection molding of the capsule 200 results in the push rod 206 being embedded therein.

Other advancement device implementations include an attachment tube disposed at a proximal end of the push rod to allow for attaching the advancement device to the guiding catheter while the catheter can be advanced over a guidewire.

Figure 13A:
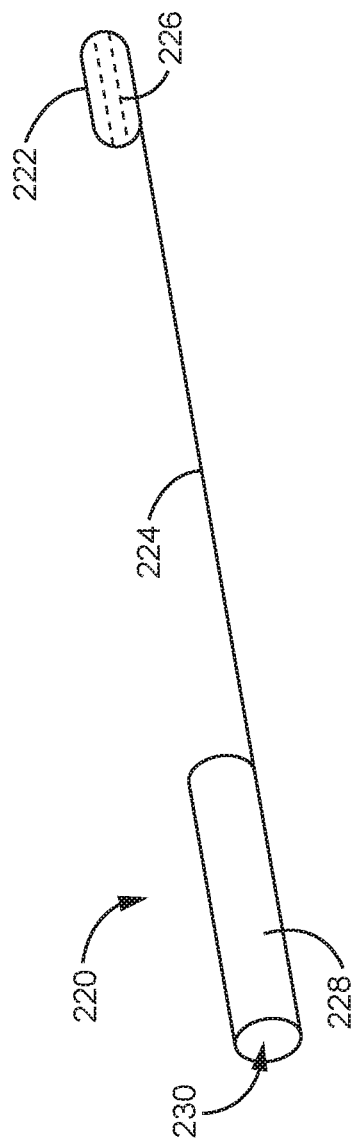
FIG. 13A is a cross-sectional side view of a catheter advancement device having an attachment tube, according to one embodiment.

For example, FIG. 13A depicts, according to one embodiment, another catheter advancement device 220 for assisting with or use in advancing a catheter, such as, for example, a cardiovascular guiding catheter. As with the other advancement device embodiments disclosed herein, the device 220 has a capsule 222 and a push rod (also referred to herein as an "elongate component") 224 coupled thereto. The capsule 222 can have a lumen 226 defined therethrough that is configured to allow for passage of a guidewire (not shown) therethrough. The various components of the device 220 are substantially similar to the various components described in the other device embodiments above and can incorporate any of the various alternative components and/or features thereof.

In addition, the push rod 224 in this implementation has an attachment tube (also referred to as a "coupling tube") 228 attached at a proximal end of the push rod 224 as shown such that a catheter valve (including any known valve on any known catheter as discussed elsewhere herein) can attach to the attachment tube 228 as desired and a guidewire can be moveably disposed therethrough. That is, the attachment tube 228 defines a lumen 230 disposed through the tube 228 as shown that is sized to slidably receive a guidewire.

In one embodiment, the lumen 274 in the tube 270 (or any lumen of any attachment tube disclosed or contemplated herein) has an inner diameter ranging from about 0.008 inches to about 0.040 inches. Alternatively, the inner diameter ranges from about 0.014 inches to about 0.030 inches. In a further alternative, the tube 270 is sized such that the lumen 274 can receive any known cardiovascular guidewire ranging in size from about 0.01 inches to about 0.04 inches.

Figure 13B:
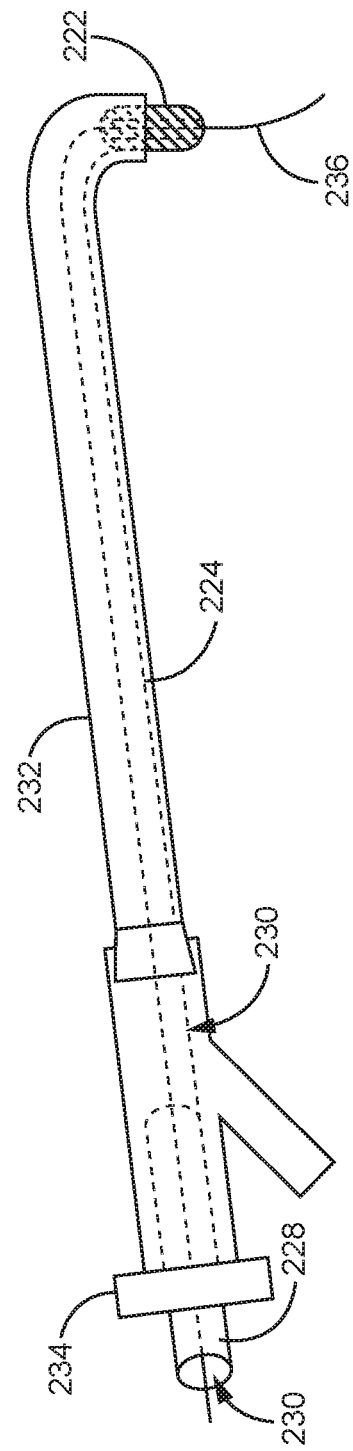
FIG. 13B is a cross-sectional side view of the catheter advancement device of FIG. 13A disposed within a guiding catheter, according to one embodiment.

In use, as best shown in FIG. 13B, according to one implementation, the advancement device 220 can be disposed in a catheter 232. The known catheter 232 has a known proximal valve 234, which is a Toughy-borst valve or any known sealable valve. It is understood that the catheter 232 can be any known cardiovascular catheter as discussed elsewhere herein. The attachment tube 228 is disposed along the length of the push rod 224 such that when the device 220 is disposed within the catheter 232 as shown with the capsule 222 extending partially out of the distal end of the catheter 232, the attachment tube 228 is disposed through the valve 234 of the catheter 232 (similar to valve 26 discussed above). Further, the attachment tube 228 can receive a guidewire 236 in the lumen 230 of the attachment tube 228 when the catheter 232 and advancement device 220 are disposed over the guidewire 236 as shown. As a result, the valve 234 of the catheter 232 can be removably coupled to the attachment tube 228 (via any known mechanism that such a valve 234 is attached to a device disposed therethrough) such that the advancement device 220 is attached to the catheter 232 and thus both are advanced together (such that the advancement device 220 does not move axially in relation to the catheter 232) while the guidewire 236 can be slidably disposed through the lumen 230 of the tube 228 such that the catheter 232 and device 220 can be moved in relation to the guidewire 236. In other words, the attachment tube 228 makes it possible for the advancement device 220 to be attached to the catheter 232 via the coupling of the catheter valve 234 to the tube 228 while the valve 234 is not attached to the guidewire 236 (because the guidewire 236 is slidably disposed through the tube 228).

Figure 14:
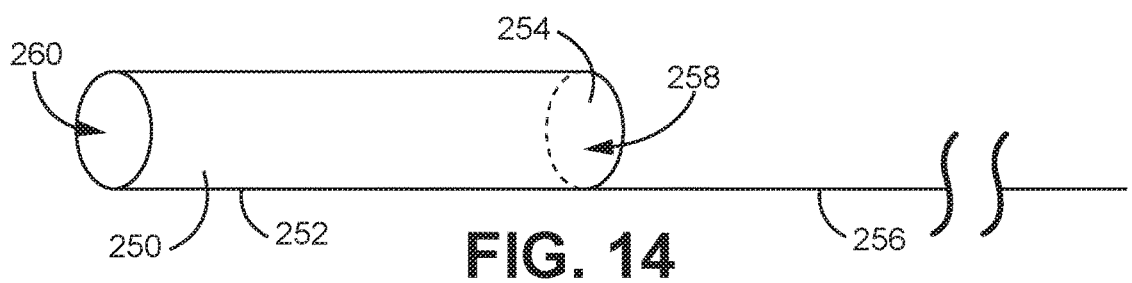
FIG. 14 is an expanded side view of an attachment tube on a catheter advancement device, according to one embodiment.

One specific embodiment of an attachment tube 250 that can be incorporated into any advancement device as disclosed or contemplated herein is depicted in FIG. 14, in accordance with one implementation. The tube 250 is coupled to a proximal end of a push rod 256 and has an elongate tubular body 252 that defines a lumen 254 as shown. The tubular body 252 has a distal opening 258 and a proximal opening 260, both of which are in fluidic communication with the lumen 254. In this implementation, the tubular body 252 is a substantially unitary body 252 having no substantial openings along the length of the body 252. As with the other attachment tube embodiments disclosed or contemplated herein, the tubular body 252 is configured to be disposed through a catheter valve (such as valve 234 discussed above) such that the valve can be attached to the body 252.

Figure 15A:
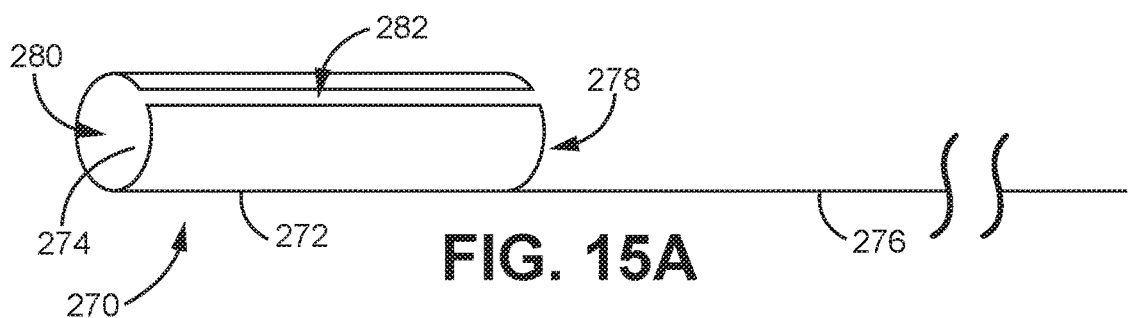
FIG. 15A is an expanded side view of another attachment tube on a catheter advancement device, according to a further embodiment.
Figure 15B:
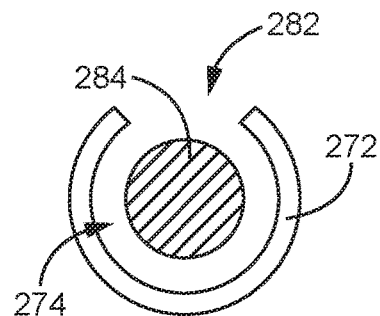
FIG. 15B is a cross-sectional view along the longitudinal axis of the attachment tube of FIG. 15A, according to one embodiment.

Another embodiment of an attachment tube 270 that can be incorporated into any advancement device as disclosed or contemplated herein is depicted in FIGS. 15A and 15B. The tube 270 is coupled to a push rod 276 and has substantially the same features and characteristics as the tube 250 discussed above, and thus the description of the similar components and features above apply equally to this tube 270 embodiment as well, except as described herein. Additionally, in this specific implementation, the tube 270 is a compressible tube 270. The specific compressible tube 270 embodiment as shown has an elongate opening 282 defined along at least a portion of the length of the body 272. More specifically, in the specific embodiment depicted in FIGS. 15A and 15B, the elongate opening 282 is a slot 282 that extends along the entire length of the body 272 from the distal opening 278 to the proximal opening 280. The tubular body 272 and slot 282 are configured such that the body 272 can be disposed through a catheter valve (such as valve 234 discussed above) such that when the valve is clamped down on the tubular body 272, the body 272 is compressed as a result of the slot 282 being collapsed by the valve such that the two opposing sides of the body 272 that define the slot 282 are urged toward each other.

In one embodiment, the slot 282 has a width that ranges from about 0.004 inches to about 0.03 inches. Alternatively, the slot 282 has a width ranging from about 0.01 inches to about 0.02 inches. In a further embodiment, the slot 282 is gap in the circumference of the body 272 such that the gap constitutes a percentage of the total circumference of the body 272 ranging from about 4 percent to about 25 percent. Regardless of the size of the slot 282, it is understood that the terms "attachment tube" and "tube" are intended herein to encompass any tubular structure having any sized slot, gap, slit, or opening defined therein, including a tubular structure having a gap that constitutes as much as 25 percent of the circumference of the structure.

Alternatively, instead of extending along the entire length of the body 272, the slot 282 can extend along a portion of the length of the body 272. In a further embodiment, the opening 282 can be any opening of any shape or configuration that allows for compression of the tubular body 272 when the valve (such as valve 234, for example) is clamped down thereon. According to another implementation, any opening 282 extending along the entire length of the body 272 can not only provide compressive qualities to the body 272, but can also assist with positioning a guidewire (such as guidewire 284 as discussed below) into the lumen 274 of the tube 270 via the opening 282. That is, rather than having to thread a guidewire into one of the openings 278, 280 and thereby through the entire length of the lumen 274, a user can insert the guidewire into the lumen 274 through the opening 282.

Regardless of the exact size, shape, and configuration of the opening 282, the body 272 of the compressible tube 270 has some degree of compliance that allows for the body 272 to be compressed such that the lumen 274 defined therein is reduced in size (or inner diameter) as a result of the compression. Thus, as best shown in FIG. 15B, the lumen 274 in the uncompressed state has sufficient size such that there is space between the inner wall of the lumen 274 and the guidewire 284. As such, the body 272 can be compressed by some amount such that the inner diameter of the lumen 274 is reduced while still providing sufficient space between the inner wall of the lumen 274 and the guidewire 284 such that the guidewire 284 can still move axially in relation to the body 272 while minimizing the amount of blood loss through the lumen 274 by minimizing the space between the inner wall of the lumen 274 and the guidewire 284.

In another alternative embodiment, the tube 270 and any other compressible tube embodiment as disclosed or contemplated herein can have any structure or feature that provides or allows for compression of the tube 270.

Figure 16:
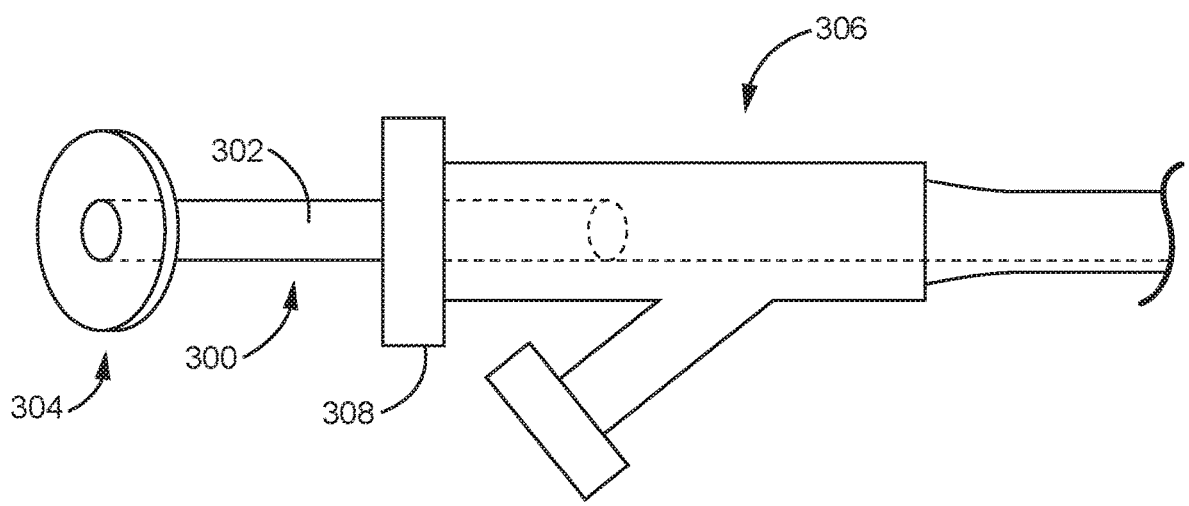
FIG. 16 is a cross-sectional side view of another catheter advancement device having an attachment tube disposed within a guiding catheter, according to another embodiment.

In accordance with another embodiment as depicted in FIG. 16, the advancement device 300 has an attachment tube 302 with a blocking protrusion 304 extending from a proximal end thereof. In this implementation, the blocking protrusion 304 is a disk 304 disposed at or near the proximal end of the tube 302. Alternatively, the blocking protrusion 304 can be a lip, a rim, or any other known structural feature or component that forms a radial protrusion or extension that is disposed at a proximal end of the attachment tube 302 and has an outer diameter or dimension that is greater than the inner diameter of the valve 308 of the catheter 306, thereby preventing the blocking protrusion 304 from passing into or through the valve 308. As such, the blocking protrusion 304 can be incorporated into the attachment tube 302 such that the advancement device 300 cannot be inadvertently advanced distally so far that the attachment tube 302 passes through the valve 308.

It is understood that any of the attachment tube embodiments disclosed or contemplated herein can be incorporated into any of the advancement devices disclosed or contemplated herein.

Alternatively, the various methods and devices disclosed or contemplated herein can be used to assist in the advancement of any type of catheter, pre-shaped or otherwise. It is understood that while many of the exemplary embodiments disclosed herein discuss cardiovascular guiding catheters, the various device implementations disclosed or contemplated herein can be used with any guiding, delivery, or other type of catheter or sheath.

Although the various implementations have been described with reference to preferred embodiments, persons skilled in the art will recognize that changes may be made in form and detail without departing from the spirit and scope thereof.

What is claimed is:

1. A method of assisting advancement of a catheter through a blood vessel, the method comprising:
   inserting an advancement assistance device into a lumen of the catheter, the advancement assistance device comprising:
   (a) an elongate shaft;
   (b) a body fixedly attached to a distal end of the elongate shaft and
   (c) an attachment tube associated with a proximal portion of the elongate shaft;
   urging the advancement assistance device distally through the lumen of the catheter until a distal portion of the body extends out of a distal opening in the catheter and the attachment tube is disposed within a proximal valve of the catheter;
   attaching the proximal valve to the attachment tube by clamping the proximal valve onto the attachment tube such that the attachment tube is compressed;
   urging the catheter distally into the blood vessel to a target site over a guidewire; and
   retracting the advancement assistance device from the catheter.

2. The method of claim 1, further comprising:
   urging the advancement assistance device distally until the body extends out of the distal opening, whereby space is provided between the body and the distal opening;
   urging contrast solution distally through the catheter and through the space between the body and the distal opening and into the blood vessel; and
   urging the advancement assistance device proximally until the distal portion of the body extends out of the distal opening in the catheter.

3. The method of claim 1, wherein the body comprises a lumen defined through the body.

4. The method of claim 3, further comprising urging contrast solution distally through the catheter and through the lumen defined in the body and into the blood vessel.

5. The method of claim 1, wherein the body comprises a channel defined longitudinally along an outer surface of the body.

6. The method of claim 5, further comprising urging contrast solution distally through the catheter and through the channel and into the blood vessel.

7. The method of claim 1, wherein the body further comprises a seating component formed around at least a portion of an outer circumference of the body.

8. The method of claim 7, further comprising:
urging the advancement assistance device distally through the lumen of the catheter until the seating component is urged out of the distal opening in the catheter; and
urging the advancement assistance device proximally until the seating component contacts the distal end of the catheter.

9. A method of assisting advancement of a catheter through a blood vessel, the method comprising:
inserting an advancement assistance device into a lumen of the catheter, the advancement assistance device comprising:
(a) an elongate shaft;
(b) a body fixedly attached to a distal end of the elongate shaft, the body comprising a guidewire lumen defined through the body, the body sized such that when the body is disposed within the catheter, an outer surface of at least a portion of the body makes contact with an inner wall of the catheter such that passage of fluid therebetween is prevented; and
(c) an attachment tube associated with a proximal portion of the elongate shaft;
urging the advancement assistance device distally into the lumen of the catheter until a distal portion of the body extends out of a distal opening in the catheter, a proximal portion of the body is positioned within the lumen of the catheter, and the attachment tube is disposed within a proximal valve of the catheter;
attaching the proximal valve to the attachment tube by clamping the proximal valve onto the attachment tube such that the attachment tube is compressed;
urging the catheter distally into the blood vessel to a target site over a guidewire; and
retracting the advancement assistance device from the catheter.

10. The method of claim 9, further comprising urging contrast solution distally through the catheter and through the guidewire lumen and into the blood vessel.

11. The method of claim 9, wherein the body further comprises a channel defined longitudinally along an outer surface of the body.

12. The method of claim 11, further comprising urging contrast solution distally through the catheter and through the channel and into the blood vessel.

13. The method of claim 9, wherein the body further comprises a seating component formed around at least a portion of an outer circumference of the body.

14. The method of claim 13, wherein the seating component comprises a lip or a ridge.

15. The method of claim 13, further comprising:
urging the advancement assistance device distally through the lumen of the catheter until the seating component is urged out of the distal opening in the catheter; and
urging the advancement assistance device proximally until the seating component contacts the distal end of the catheter.

16. A method of assisting advancement of a catheter through a blood vessel, the method comprising:
inserting an advancement assistance device into a lumen of the catheter, the advancement assistance device comprising:
(a) an elongate shaft;
(b) a body associated with a distal end of the elongate shaft; and
(c) an attachment tube associated with a proximal portion of the elongate shaft;
urging the body distally into the lumen of the catheter until a distal portion of the body extends out of a distal opening in the catheter;
attaching the proximal valve to the attachment tube by clamping the proximal valve onto the attachment tube; and
urging the catheter distally into the blood vessel to a target site over a guidewire.

17. The method of claim 16, wherein the body comprises a lumen defined through the body.

18. The method of claim 17, further comprising urging contrast solution distally through the catheter and through the lumen defined in the body and into the blood vessel.

19. The method of claim 16, wherein the body comprises a channel defined longitudinally along an outer surface of the body.

20. The method of claim 19, further comprising urging contrast solution distally through the catheter and through the channel and into the blood vessel.

\* \* \* \* \*